United States Patent [19]

Fehr

[11] 4,431,827
[45] Feb. 14, 1984

[54] PENTADECANOLIDE DERIVATIVES

[75] Inventor: Charles Fehr, Versoix, Switzerland

[73] Assignee: Firmenich S.A., Geneva, Switzerland

[21] Appl. No.: 365,336

[22] Filed: Apr. 5, 1982

[30] Foreign Application Priority Data

Apr. 21, 1981 [CH] Switzerland .......................... 2593/81

[51] Int. Cl.³ .......................................... C07D 313/00
[52] U.S. Cl. ..................................... 549/271; 568/354; 568/375
[58] Field of Search ......................................... 549/271

[56] References Cited

U.S. PATENT DOCUMENTS 3,418,290 12/1968 Bantjes ................................ 549/271
3,728,358 4/1973 Mookherjee et al. .............. 549/271

Primary Examiner—Jane T. Fan
Attorney, Agent, or Firm—Pennie & Edmonds

[57] ABSTRACT

Novel lactonic derivatives and their use as starting materials for preparing macrocyclic hydroxyketones useful as intermediates in the preparation of fragrant compounds.

1 Claim, No Drawings

PENTADECANOLIDE DERIVATIVES

SUMMARY OF THE INVENTION

The invention refers to novel compounds of formula

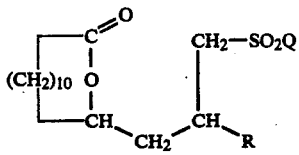 (II)

wherein symbol R represents a hydrogen atom or a methyl radical and Q represents an aryl or alkyl radical.

The invention also refers to a process for preparing a compound of formula

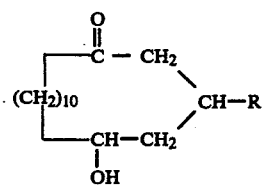 (I)

wherein R represents a hydrogen atom or a methyl radical, which comprises treating a compound of formula (II) as defined hereinabove with a strong base and subsequently reducing the resulting product.

BACKGROUND OF THE INVENTION

EXALTONE® and muscone, two macrocyclic ketones, are very appreciated in the art of perfumery for their elegant and tenacious musky odour. Both compounds have been known for several decades and since their discovery a variety of syntheses have been proposed and described in the scientific literature [see e.g.: J. Chem. Soc. 1964, 4154; Tetrahedron 20, 2601 (1964); Helv. Chim. Acta 50, 705 (1967) and Helv. Chim. Acta 50, 708 (1967)]. So far, however, most of the published methods could not be successfully applied to their industrial scale preparation, especially in view of their complexity or in view of the low yields achieved in the critical reaction steps.

One of the prior known syntheses [Helv. Chim. Acta 50, 705 (1967)] makes use of the compound of formula

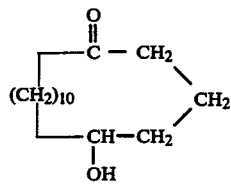 (Ia)

(R=H, in formula I) as intermediate in the synthesis of EXALTONE® (cyclopentadecanone), and of the corresponding methyl derivative of formula

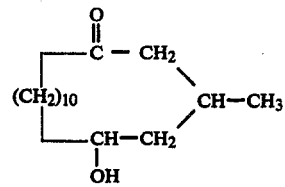 (Ib)

(R=methyl, in formula I) in the synthesis of muscone. Both intermediate compounds can be obtained from cyclododecanone by a condensation reaction and a subsequent cyclization, ozonolysis, hydrogenation and dehydration. Due to the rather poor overall yields achieved, however, such synthetic routes have not been developed industrially.

The advantage of the invention consists in providing a new and original synthetic process for preparing the above mentioned intermediate hydroxyketones of formula (I), thus making the preparation of the desired macrocycles more convenient and industrially feasible.

PREFERRED EMBODIMENTS OF THE INVENTION

In formula (II) given above, symbol Q represents preferably a lower alkyl radical such as for instance a methyl, ethyl, propyl or butyl radical, or an aryl radical such as phenyl or p-tolyl.

According to the invention, compounds (II) are treated first with a strong base, in the presence of an inert organic solvent or mixture of solvents. As strong base, one can advantageously use an alkali metal alkoxide such as potassium tert-butoxide for example, or an alkali metal amide such as sodium amide in the presence of liquid ammonia or sodium 2-amino-ethylamide in the presence of ethylene-diamine for example. Sodium amide in liquid $NH_3$ is preferred; it is used in the presence of tetrahydrofuran.

The said strong base is generally used in excess, at the rate of about 2 to 3 equivalents of base for 1 equivalent of compound (II).

When considered under its formal aspect, the said basic treatment consists in a cyclization reaction followed by a hydrolysis yielding to intermediate compounds of formula

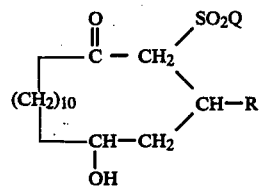 (III)

(R=H or $CH_3$; Q=aryl or alkyl) whih can be, if necessary, isolated from the reaction mixture. Compounds (III) are novel compounds.

For practical and economical reasons however, basic treatment and subsequent reduction are effected in one single reaction step. The said reduction can be effected by adding an alkali metal or an Al-Hg amalgam to the reaction mixture, according to the techniques usual in the art. Sodium metal is the preferred reducing agent.

Compounds (II) used as starting materials in the above process are also novel compounds. They can be easily prepared from 2-allyl-cyclododecanone or 2-methylallyl-cyclododecanone respectively, after radical initiated addition of the appropriate thiol and subsequent oxidation according to the Bayer-Villiger method. Both reactions can be effected in accordance with the usual techniques and are illustrated by the following reaction scheme

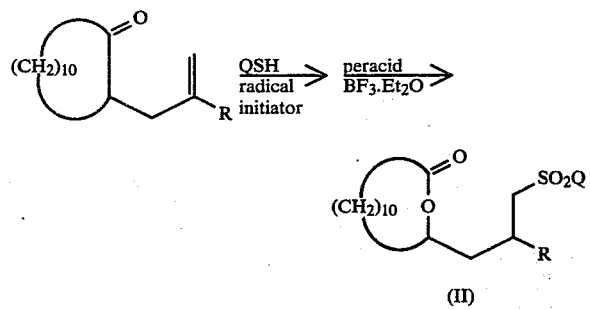

(R=H or CH₃; Q=aryl or alkyl). The examples given hereinafter will illustrate the invention in a more detailed manner. In the said examples, the temperatures are indicated in degrees centigrade and the abbreviations used possess the sense common in the art.

EXAMPLE 1

15-Phenylsulfonyl-12-pentadecanolide 22.0 g (100 mmole) of 2-allyl-cyclododecanone—Helv. Chim. Acta 54, 2889 (1971)—in admixture with 13.2 g (12.2 mmole) of thiophenol and 0.3 g of α,α′-azoisobutyronitrile were heated at 100° for 10 hours, an additional amount of 0.6 g of α,α′-azoisobutyronitrile being added over this period, portionwise, to the reaction mixture. After elimination of the excess of thiophenol and unreacted 2-allyl-cyclododecanone (2.25 g) by distillation (170°/0.05 Torr) the reaction mixture was diluted with 300 ml of trichloroethane and cooled to 0°. 90.4 g (475 mmole) of 40% peracetic acid were then progressively added to the above solution under good stirring (reaction temperature: 30°-40°). After addition of 7.5 g (53 mmole) of BF₃.Et₂O, the resulting mixture was further stirred for 10 days at 50°, 4 portions each of 11.3 g (60 mmole) of 40% peracetic acid being added thereto over this period. After cooling to 20°, the reaction mixture was poured onto crushed ice and then brought to pH 8 by the addition of 10% aqueous sodium hydroxide. After washing with a 10% solution of NaHSO₃ in water, then with H₂O, the organic phase was dried over Na₂SO₄ and evaporated. The obtained residue was finally purified by column chromatography (silicagel—eluent: 50/50 mixture of petrol ether and ethyl acetate) to afford 27.7 g (81% yield based on transformed 2-allyl-cyclododecanone) of the title compound (purity 90%).

IR: 2920, 1720, 1450, 1300, 1240, 1140 cm⁻¹;

NMR: 1.10–2.00 (22H, m); 2.31 (2H, m); 3.15 (2H, m); 4.92 (1H, m); 7.50–8.02 (5H, m) δ ppm.

EXAMPLE 2

14-Methyl-15-phenylsulfonyl-12-pentadecanolide 15.6 g (66 mmole) of 2-methallyl-cyclododecanone—Chem. Comm. 1976, 1021—and 8.7 g (79 mmole) of thiophenol were heated at 100°-110° for 48 hours, in the presence of 0.6 g of α,α′-azoisobutyronitrile. The resulting mixture was then treated with 40% peracetic acid and BF₃.Et₂O as indicated in Example 1 to afford 20.1 g (78% based on converted 2-methallyl-cyclododecanone) of the title compound (purity 90%).

IR: 2930, 1720, 1445, 1300, 1245, 1145, 1085 cm⁻¹;

NMR: 1.09 (3H, d, J=6 Hz); 1.05–2.00 (21H, m); 2.25 (2H, m); 4.96 (1H, m);

7.50–8.03 (5H, m) δ ppm;

MS: M+: 394(0.2); m/e=376(6), 366(6), 253(15), 168(24), 143(15), 125(18), 111(26), 98(55), 83(42), 69(61), 55(93), 43(100).

EXAMPLE 3

Preparation of 5-hydroxy-pentadecanone (a) intermediate compound not isolated

A solution of 6.3 g (14.9 mmole) of the compound of Example 1 in 100 ml of tetrahydrofuran (THF) was added dropwise to a solution of 46.8 mmoles of sodium amide in 600 ml liquid NH₃ (temperature: −40° to −45°). After stirring of the reaction mixture over a period of 20 minutes, 1.08 g (46.8 m atom-g) of sodium metal were added thereto, portionwise. 30 minutes after this addition, 200 ml of an aqueous solution of NaCl were added dropwise to the reaction mixture, this latter being finally extracted with ethyl acetate. After washing with brine, drying over Na₂SO₄ and evaporation, there were obtained 4.0 g of crude material.

An analytical sample was purified by column chromatography (silicagel—eluent: 4/1 mixture of cyclohexane and ethyl acetate): 60% yield. The thus purified compound was found identical with a sample prepared according to the literature [Helv. Chim. Acta 50, 705 (1967)].

The crude material obtained hereinabove was converted into cyclopentadecanone (EXALTONE®) in accordance with the process given in the above cited literature.

(b) intermediate compound isolated 10 g of the compound of Example 1 were treated with sodium amide in liquid ammonia according to the process of letter (a) above to afford, after extraction and purification, a compound having the formula

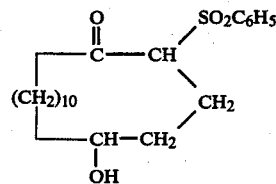

(80% yield), m.p. 135°–136° (cryst. in ether).

IR: 3630, 2960, 1720, 1450, 1310, 1150, 1080 cm⁻¹;

NMR: 1.10–2.50 (23H, m); 2.77 (2H, t, J=6 Hz); 3.40 (1H, m); 4.22 (1H, m);

7.45–7.94 (5H, m) δ ppm;

MS: M+: 380(1); m/e: 362(16), 239(33), 221(30), 169(23), 141(41), 125(27), 109(20), 95(39), 77(100), 55(96), 41(88).

The intermediate compound thus prepared was then reduced with sodium metal in liquid ammonia as indicated sub letter (a) to afford, after purification by column chromatography (silicagel—eluent: 7/3 mixture of cyclohexane and ethyl acetate) the title compound in a 81% yield.

EXAMPLE 4

Preparation of 5-hydroxy-3-methyl-pentadecanone (a) intermediate compound not isolated 13.1 g (30 mmole) of the compound of Example 2, in solution in a THF/liquid $NH_3$ mixture were treated in accordance with the process of Example 3, letter (a), to afford 10.2 g of crude material.

An analytical sample was purified by column chromatography (silicagel—eluent: 7/3 mixture of cyclohexane and ethyl acetate): 51% yield. The compound thus obtained was found identical with a sample prepared according to the literature [Helv. Chim. Acta 50, 705 (1967)]. The crude material obtained hereinabove was converted into 3-methyl-cyclopentanone (muscone) in accordance with the process described in the above cited literature.

(b) intermediate compound isolated 10 g of the compound of Example 2 were treated with sodium amide in liquid $NH_3$ according to the process of letter (a) above to afford, after extraction and purification by column chromatography (silicagel—eluent: 4/1 mixture of cyclohexane and ethyl acetate), a compound having the formula

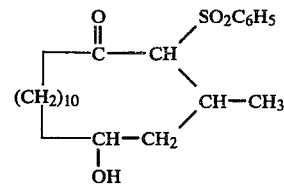

(80% yield).

IR: 3580, 2950, 1715, 1450, 1310, 1150 $cm^{-1}$.

The intermediate compound thus prepared was then reduced with sodium metal in liquid ammonia as indicated sub letter (a) to afford, after purification by column chromatography (silicagel—eluent: 7/3 mixture of cyclohexane and ethyl acetate) the title compound in a 69% yield.

What I claim is:

1. A compound of the formula

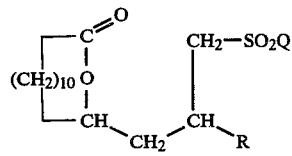

where symbol R represents a hydrogen atom or a methyl radical and Q represents a lower alkyl, phenyl or p-tolyl radical.

* * * * *

UNITED STATES PATENT AND TRADEMARK OFFICE
CERTIFICATE OF CORRECTION

PATENT NO. : 4,431,827
DATED : February 14, 1984
INVENTOR(S) : Charles Fehr

It is certified that error appears in the above-identified patent and that said Letters Patent are hereby corrected as shown below:

Col. 1, the formula appearing between lines 10 and 15 should be as follows:

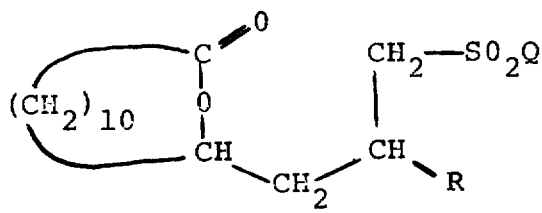

Col. 1, the formula appearing between lines 21 and 30 should be as follows:

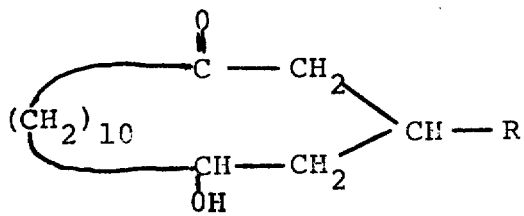

Col. 1, the formula appearing between lines 56 and 64 should be as follows:

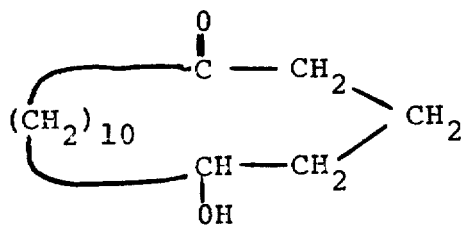

UNITED STATES PATENT AND TRADEMARK OFFICE
CERTIFICATE OF CORRECTION

PATENT NO. : 4,431,827
DATED : February 14, 1984
INVENTOR(S) : Charles Fehr

It is certified that error appears in the above-identified patent and that said Letters Patent are hereby corrected as shown below:

Col. 2, the formula appearing between lines 1 and 9 should be as follows:

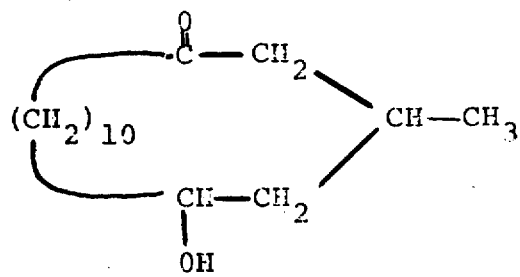

Col. 2, the formula appearing between lines 46 and 55 should be as follows:

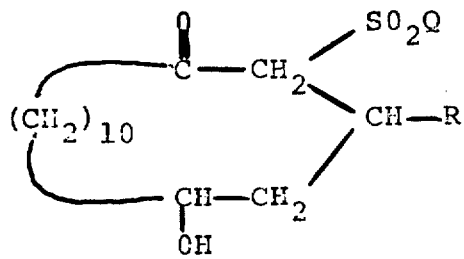

UNITED STATES PATENT AND TRADEMARK OFFICE
CERTIFICATE OF CORRECTION

PATENT NO. : 4,431,827
DATED : February 14, 1984
INVENTOR(S) : Charles Fehr

It is certified that error appears in the above-identified patent and that said Letters Patent are hereby corrected as shown below:

Col. 4, the formula appearing between lines 45 and 52 should be as follows:

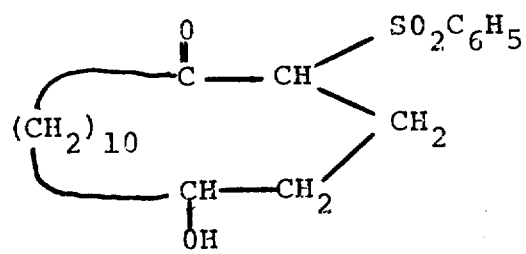

Col. 6, the formula appearing between lines 1 and 9 should be as follows:

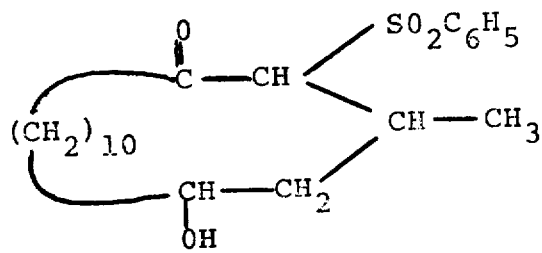

UNITED STATES PATENT AND TRADEMARK OFFICE
CERTIFICATE OF CORRECTION

PATENT NO. : 4,431,827

DATED : February 14, 1984

INVENTOR(S) : Charles Fehr

It is certified that error appears in the above-identified patent and that said Letters Patent are hereby corrected as shown below:

Col. 6, the formula appearing between lines 21 and 28 should be as follows:

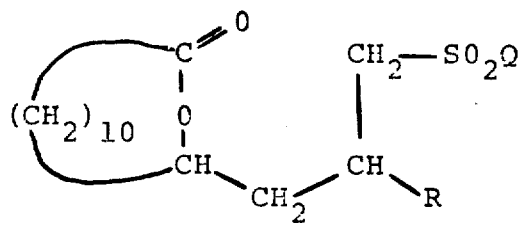

Signed and Sealed this

Twenty-fifth Day of September 1984

[SEAL]

Attest:

Attesting Officer

GERALD J. MOSSINGHOFF

Commissioner of Patents and Trademarks